United States Patent [19]

Compere et al.

[11] 4,445,908

[45] May 1, 1984

[54] EXTRACTING ALCOHOLS FROM AQUEOUS SOLUTIONS

[75] Inventors: Alicia L. Compere, Knoxville; John M. Googin; William L. Griffith, both of Oak Ridge, all of Tenn.

[73] Assignee: The United States of America as represented by the United States Department of Energy, Washington, D.C.

[21] Appl. No.: 326,775

[22] Filed: Dec. 2, 1981

Related U.S. Application Data

[63] Continuation-in-part of Ser. No. 212,005, Dec. 1, 1980, abandoned.

[51] Int. Cl.$^3$ ............................................. C10L 1/22
[52] U.S. Cl. ........................................... 44/56; 44/51
[58] Field of Search ..................... 44/56, 51; 252/308

[56] References Cited

U.S. PATENT DOCUMENTS

| | | | |
|---|---|---|---|
| 2,807,525 | 9/1957 | Foreman | 44/77 |
| 2,979,528 | 4/1961 | Lundsted | 548/312 |
| 3,036,118 | 5/1962 | Jackson et al. | 560/182 |
| 4,046,519 | 9/1977 | Piotrowski | 44/51 |
| 4,158,551 | 5/1979 | Feuerman | 44/51 |
| 4,182,614 | 1/1980 | Moriyama et al. | 44/51 |

*Primary Examiner*—Charles F. Warren
*Assistant Examiner*—Mrs. Y. Harris-Smith
*Attorney, Agent, or Firm*—Edwin D. Grant; Stephen D. Hamel; Michael F. Esposito

[57] ABSTRACT

Hydrocarbon and surfactants are contacted with a solution of alcohol and water to extract the alcohol into the hydrocarbon-surfactant mixture.

13 Claims, No Drawings

EXTRACTING ALCOHOLS FROM AQUEOUS SOLUTIONS

This invention, which was made under a contract with the U.S. Department of Energy, relates to a method for separating alcohols from fermentation solutions and, more particularly, is concerned with the extraction of alcohols from fermentation solution into hydrocarbon mixtures through the addition of a polyoxyalkylene polymer. A resultant mixture consisting of hydrocarbon, alcohol(s), polyoxyalkylene polymer, and water can be directly added to fuels or further purified to make the alcohols more useful.

BACKGROUND OF THE INVENTION

This application is a continuation-in-part of patent application Ser. No. 212,005 filed on Dec. 1, 1980, now abandoned.

To conserve our rapidly dwindling supply of petroleum, a fuel mixture of alcohol and gasoline is being marketed for use in motor vehicles. The alcohol, usually ethanol or methanol, used for this fuel is often distilled from water-alcohol solutions and blended with an appropriate fuel. Purification of ethanol or methanol by the conventional procedure frequently requires the input of more energy for distillation than is obtained in the alcohol product. Direct formation of a fuel by extraction of alcohol from an organic fermentation liquor into a petroleum derivative has been suggested heretofore, but this fuel-forming method has, thus far, been impracticable because of low extraction efficiencies. If the amount of alcohols removable from an aqueous fermentation liquor by extraction into a petroleum base fuel could be increased significantly, fuel mixtures containing of alcohols combined with gasoline, diesel fuel and fuel oil would become more widely used as a means for conserving petroleum supplies.

The invention disclosed herein is concerned with the extraction of alcohols with 2 to 4 carbons from fermentation solutions into hydrocarbon mixtures through the addition of an polyoxyalkylene polymer and a small amount of hydrocarbon. A resultant mixture consisting of hydrocarbon, alcohol(s), or ketone(s), polyoxyalkylene polymer, and water can be directly added to fuels or further purified. Where the polyoxyalkylene polymer-alcohol combination is suitable for use in enhanced oil recovery, it may be possible to use the mixture directly for injection.

One use of the emulsified alcohol-water-surfactant-ketone mixture would be in fuels. In would be particularly desirable from the point of energy conservation if this material could be directly used in fuels. Although there is not a large amount of overlap in the surfactants which we have used, it appears, based on prior art, that use of our product in fuels directly in a stable form is possible.

PRIOR ART

Some prior art makes reference to use of surfactant materials in fuels. Such use can improve the pollution characteristics of the fuel through the addition of small amounts of water and small alcohols, such as methanol and ethanol. This can be illustrated by the patent of Wenzl and Steinmann (U.S. Pat. No. 4,083,698) which claimed a fuel composition comprising a water in oil emulsion of (a) a hydrocarbon fuel, (b) water, (c) preferably a water soluble alcohol, and (d) a combination of surfactants to provide a clear composition stable against phase separation over a wide range of temperatures. The surfactant mixture in this case comprises a saturated or unsaturated long chain fatty acid salt having 12 to 18 carbon atoms or a mixture thereof, a free unsaturated long chain fatty acid having from 12 to 18 carbon atoms or a mixture of free unsaturated and saturated long chain fatty acids having from 12 to 18 carbon atoms, and a non-ionic surfactant. A previous patent, U.S. Pat. No. 4,002,435, used only the fatty acid-fatty acid salt mixture. The amount of water used may be up to around 20% of the total fuel mixture. The hydrocarbon mixtures used were both gasoline and diesel fuel. However, it is reasonable to expect that other mixed hydrocarbon fuels, such as fuel oils, coal oils, and various pyrolysis-produced oils, will also be suitable for use. Alcohols ranged in chain length from 1 to 6 carbons, and ketones were included in some fuel mixtures.

Another patent, U.S. Pat. No. 4,046,519 (Piotrowski 1977), indicates that methanol, water, gasoline, and a surfactant can be blended to form a stable microemulsion. In this case, the hydrophile-lipophile balance, HLB, rather than specific structure, is used to define the suitable surfactant. The fuels specified included gasoline, diesel, home heating oil, and aviation gasoline. Although methanol is not involved directly in this invention, it is important to remember that this illustrates the fact that alcohols of 1 to 6 carbons can be used in microemulsion fuels.

Based on the prior art, it appears that the surfactant emulsions which are formed as a part of alcohol removal can be incorporated, without removal of water, or surfactant, directly into hydrocarbon fuels which are stable during storage and used. Based on the prior open literature it appears that emulsions of water in diesel fuel provide for increased consumer safety by reducing the risk of explosion, and also, under proper emulsion conditions, reduce the amount of oxides of nitrogen and particulate smoke produced by diesel engines.

SUMMARY OF THE INVENTION

It is an object of this invention to provide an efficient process for extracting alcohols from a fermentation solution containing the same into hydrocarbon fuel mixtures, such as gasoline, diesel fuel and fuel oil.

The above stated object is achieved in accordance with a preferred embodiment of the invention by contacting an aqueous fermentation liquor with a hydrocarbon or hydrocarbon mixture containing carbon compounds having 5-18 carbon atoms, which may include gasoline, diesel fuel or fuel oil. The hydrocarbon-aqueous alcohol solution is mixed in the presence of one or more of a group of polyoxyalkylene polymers described in detail hereinafter, thereby efficiently extracting the fermentation alcohol into the hydrocarbon fuel-polyoxyalkylene polymer mixture.

DETAILED DESCRIPTION

A preferred source of alcohol for use in forming a fuel mixture in accordance with this invention is one of the aqueous solutions obtained by fermentation. Specific examples of fermentation products useful for the purpose of the invention are described in the report titled "Evaluation of Substrates for Butanol Production", published by A. Compere and W. Griffith in Volume 20 of *Developments in Industrial Microbiology*, a 1979 publication of the Society for Industrial Microbiology. Suitable fermentation products useful in the extraction process of the invention will typically contain about 1% through 20% by volume of a mixture of acetone, ethanol, isopropanol, and n-butanol in an aqueous solution. To perform the extraction, a fermentation solution is contacted with a hydrocarbon or a mixture of hydrocarbons preferably derived from petroleum, including gasoline, diesel fuel, n-heptane and toluene, and a polyoxyalkylene polymer surface active agent which may be polyethylene glycol, polypropylene glycol, or one of the types described hereinafter.

It is to be understood that the surfactants described herein are actually commercial mixtures whose average properties are expressed generally by the formulas given. The surfactants consist of polyoxyalkylene units of variable chain length and in the formulas that are given, the numbers for these units represent average values. Although these compositions and structures may vary measurably from batch to batch, it is expected that the results obtained will be generally unchanged by use of the commercially available polyoxyalkylene surfactants. These surfactants are described in greater detail in ORNL report CONF-801212, available from National Technical Information Service, Springfield, VA 22161.

Type 1. Polymers of polyoxyethylene and polyoxypropylene having the general formula

wherein $R_1$ and $R_2$ may be H, alkane groups,

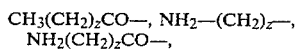

and x, y and z are variable average numbers, e.g., x may vary from 1.25 to 100, y may have a value up to 100, and z may vary from 1 to 40. As used herein and below, the subscripts x, y and z may have different values when used more than once.

An example of this type of polyoxyethylene-polyoxypropylene polymer is marketed by RASF—Wyandotte under the trademark designation Pluronic and is described in U.S. Pat. No. 2,674,619. These compounds are characterized by having all of the oxyethylene in polyoxyethylene blocks and all of the oxypropylene in polyoxypropylene blocks and the molecular weights of the polymers range from 200 to 12,500.

Type 2. Polymers of polyxoethylene and polyoxypropylene having the general formula

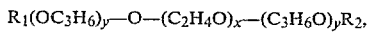

wherein $R_1$ and $R_2$ may be H, alkane groups,

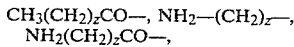

and x, y and z are variable average numbers, e.g., y may vary from 7.6 to 23.4, x may vary from 14.2 to 163.6, and z may vary from 2 to 22.

An example of this type of polyoxyethylene-polyoxypropylene polymer is marketed by BASF—Wyandotte under the trademark designation Pluronic R and is described in U.S. Pat. No. 3,036,118. The molecular weight of the polymer can be as high as approximately 25,000.

Type 3. Polymers of polyoxyethylene and polyoxypropylene having the formula

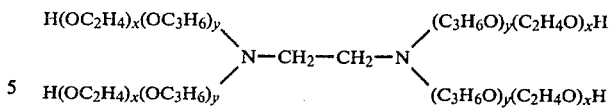

wherein x and y are variable average numbers, e.g., y may vary from 4.1 to 32.2 and x may vary from 1.9 to 124.7.

An example of this type of polyoxyethylene-polyoxypropylene polymer is marketed by BASF—Wyandotte under the trademark designation Standard Tetronic and is described in U.S. Pat. No. 2,979,528. Molecular weights for these compounds range from 1,650 to 27,500.

Type 4. Polymers of polyoxyethylene-polyoxypropylene having the formula

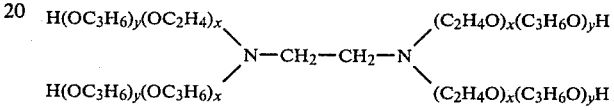

wherein x and y are variable average numbers, e.g., x may vary from 1.3 to 28.3 and y may vary from 4.1 to 32.2.

An example of this type of polyoxyethylene-polyoxypropylene polymer is marketed by BASF—Wyandotte under the trademark designation Tetronic R and is described in U.S. Pat. No. 2,979,528. Molecular weights for these compounds range from 1,240 to 12,500.

Type 5. Ethoxylated alkane and alkene acid compounds having the formula

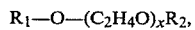

wherein $R_1$ is a fatty acid acyl group, $R_2$ is H or a fatty acid acyl group, and x is a number varying from 4 to 23.

Compounds of this type are marketed by Armak, Emery and ICI Americas, and their molecular weights range from 462 to 1,298. Weight percent hydrophile ranges from 26 to 78. Both saturated and unsaturated acids have been used as $R_1$ and $R_2$. Both single acid groups and mixed acid groups can be present, and some of the acids (such as abietic, neoabietic and rosin acids) of mixed acid tall oil groups contain aromatic rings. As is the case in previously described types, it is possible to use materials other than hydrogen as end caps, and various manufacturers do so.

Type 6. Fatty acid derived amine ethoxylates having the formula

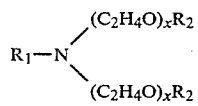

wherein $R_1$ is an alkane group having up to 18 C atoms, $R_2$ is H or the same general type of alkane as $R_1$, and x has an average value in the range of 2 to 10.

Compounds of this type are marketed by Armak, e.g., under the trademark designation Ethomeen 0/15 wherein $R_1$ is $C_{18}H_{35}$, $R_2$ is H, and x is 2.5.

Type 7. Triol chain compounds having the general formula

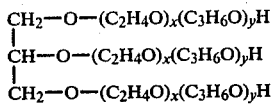

where x and y are variable average numbers, and the sum of x and y may range from 3 to 18.

Type 8. Alditol ethoxylated fatty acid compounds having the formula

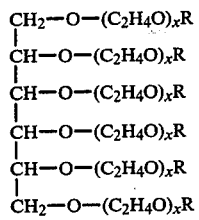

where R may be tall oil acid acyl groups and x is a variable average number, e.g., x may range from 1 to 25.

The alditol ethoxylated fatty acids are commonly used in surfactants and generally consist of a sugar alcohol structure to which are attached polyoxyethylene chains and fatty acid groups, either as esters or ethers. The R groups directly on the chains can be hydrogen or other groups. Several alditols are used, including sorbitol, mannitol, and other hexitols. The alditols studied ranged in molecular weight from 3,630 to 4,010 and contained 51 to 54.5 percent hydrophile. Acids esterified to the polyoxyethylene chains include a broad range of saturated and unsaturated fatty acids and a number of aromatic ring acids.

Type 9. Butoxylated fatty acid ester compounds having the formula

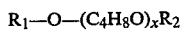

wherein $R_1$ and $R_2$ may be H, an alkane group, or $CH_3CO-$ through $C_{17}H_{35}CO-$, and an average value for x may vary from 2 to 100.

Type 10. Ethoxylated mixed chain compounds having the general formula

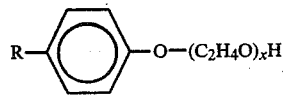

where x is a variable number, e.g., an average value for x may vary from 2 to 25.

An example of this type of compound is marketed by GAF under the trademark designation Igepal CO-530, which contains 54.8 percent hydrophile, or six repeating groups of polyoxyethylene. R in the formula may be an alkane group containing up to 9 carbon atoms and the end cap is hydrogen.

In this ethoxylated mixed chain the molecule consists of an alkane tail hooked to an aromatic ring group followed by a polyoxyethylene group and end cap.

The materials included in the above-described Types 1–10 have in common the presence of at least one polyoxyalkylene chain having a repeating unit containing two to four carbons. They have various chain end caps and structures, and fairly wide molecular weights and polyoxyalkylene contents relating thereto.

Hydrophile-lipophile balance is a measure used to describe the tendencies of surfactants to preferentially extract into oil and water. The HLB's used ranged from 0.5 to 32.

Tests were performed to determine the efficacy of the herein identified surfactants as a means for extracting ethyl, isopropyl and n-butyl alcohols from aqueous solutions of different alcohol concentration when said surfactants were combined with hydrocarbon compounds of the type included in gasoline. Ethanol, isopropanol and n-butanol were selected for the tests because they are typically present in fermentation liquors. The hydrocarbons selected for the tests were n-heptane, decane, dodecane, toluene, gasoline, diesel fuel and fuel oil. In each test which was performed, a 10 ml portion of a selected aqueous alcohol solution was contacted in a glass flask with measured amounts of a particular hydrocarbon and one or more of the selected surfactants. Several glass beads were placed in each flask to promote mixing of its contents, and the flasks were shaken at room temperature (about 20° C.) or at 37° C. for two hours. It will be noted here that higher extraction coefficients with the same surfactants were obtained at the higher temperature. Contents of the flasks were then thoroughly emulsified either by agitation with a Vortex Genie model K-550-G mixer on a setting of 10 or by being pushed in and out of a Comstock 10 ml syringe pipette with a 4 inch No. 14 cannula. Eight ml of liquid were transferred from each flask to a test tube, and the tubes were centrifuged at 7,000 rpm in a Sorvall GSA rotor. After centrifugation, liquid in each tube lighter than the aqueous phase was removed, and the aqueous phase was analyzed by means of a Varian 1520B gas chromatograph equipped with a CDS 111 data and control system and a Model 8000 autosampler. Alcohols in the samples were separated using a ⅛ inch × 10 ft. Porapak P column at 160° C. Control samples were tested concurrently to ensure accuracy in the tests, both with alcohol and hydrocarbons. Alternative equipment used in some of the tests gave equivalent results.

In the test examples, mixtures of alcohols and hydrocarbons obtained by contacting the hydrocarbons and the described surfactants with water and alcohol were relatively stable liquids, which is of course a requirement for alcohol-hydrocarbon mixtures used as fuels.

The following tables summarize tests conducted with surfactants of the different types described above. In each test 10 ml of a standard aqueous alcohol solution (AQ) were mixed with a particular hydrocarbon (HC) and a particular surfactant, the latter two components being identified in the tables. The standard aqueous alcohol solution consisted of 5 gm of a mixture of n-butanol, isopropanol and ethanol, in the ratio of 7:3:1 (which ratio was selected as representative of the amounts of the alcohols typically found in aqueous alcohol fermentation solutions), in 100 ml of water.

TABLE I

Surfactant Polyethylene glycol
(Approximate molecular weight 200)
Representative of Type 1 compounds described hereinbefore wherein x has a value of 0

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 10 | 0.25 | 26 | 27 | 29 |
| n-heptane | 10 | 0.10 | 28 | 30 | 32 |
| n-heptane | 0.1 | 0.25 | 17 | 13 | 13 |

TABLE II

Surfactant Polyethylene glycol
(Approximate molecular weight 4,000)
Representative of Type 1 compounds described hereinbefore wherein x has a value of 0

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 5 | 0.5 | 38 | 42 | 59 |

TABLE III

Surfactant Polyethylene glycol
(Approximate molecular weight 8,000)
Representative of Type 1 compounds described hereinbefore wherein x has a value of 0

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 10 | 0.25 | 28 | 29 | 30 |
| n-heptane | 1 | 0.25 | 10 | 9 | 10 |
| n-heptane | 0.1 | 0.25 | 24 | 21 | 20 |
| gasoline | 1 | 0.25 | 17 | 14 | 13 |

TABLE IV

Surfactant Polyethylene glycol
(Approximate molecular weight 2,000)
Representative of Type 1 compounds described hereinbefore wherein x has a value of 0

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 10 | 1.0 | 4 | 6 | 16 |
| n-heptane | 0.1 | 0.25 | 24 | 20 | 22 |

TABLE V

Surfactant Polyethylene glycol
(Approximate molecular weight 4,000)
Representative of Type 1 compounds described hereinbefore wherein x has a value of 0

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 1 | 10 | 2 | 5 | 15 |
| diesel oil | 1 | 0.25 | 19 | 16 | 20 |
| furnace oil | 1 | 0.25 | 16 | 12 | 16 |

TABLE VI

Surfactant $H(OC_2H_4)_{2.3}-O-(C_3H_6O)_{31}-(C_2H_4O)_{2.3}H$
Representative of Type 1 compounds described hereinbefore

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 5 | 0.5 | 30 | 31 | 30 |
| Diesel oil | 1 | 0.25 | 15 | 16 | 21 |
| furnace oil | 1 | 0.25 | 12 | 12 | 16 |

TABLE VII

Surfactant $H(OC_2H_4)_{5.7}-O-(C_3H_6O)_{34.5}-(C_2H_4O)_{5.7}H$
Representative of Type 1 compounds described hereinbefore

| Hydro-carbon | Volume of Hydro-carbon (ml) | Surfactant Con-centration % w/v AQ | Removal % Ethanol | % Iso-propanol | % Butanol |
|---|---|---|---|---|---|
| diesel oil | 1 | 0.25 | 19 | 15 | 20 |

TABLE VIII

Surfactant $H(OC_2H_4)_{11.4}-O-(C_3H_6O)_{69}-(C_2H_4O)_{11.4}H$
Representative of Type 1 compounds described hereinbefore

| Hydro-carbon | Volume of Hydro-carbon (ml) | Surfactant Con-centration % w/v AQ | Removal % Ethanol | % Iso-propanol | % Butanol |
|---|---|---|---|---|---|
| decane | 1 | 0.25 | 10 | 9 | 13 |
| n-heptane | 5 | 0.5 | 30 | 37 | 27 |
| diesel oil | 1 | 0.25 | 19 | 14 | 20 |

TABLE IX

Surfactant $H(OC_2H_4)_{16.9}-O-(C_3H_6O)_{59.8}-(C_2H_4O)_{16.9}H$
Representative of Type 1 compounds described hereinbefore

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 10 | 0.25 | 28 | 29 | 34 |
| n-heptane | 1 | 0.25 | 8 | 10 | 18 |
| diesel oil | 1 | 0.25 | 19 | 15 | 20 |
| furnace oil | 1 | 0.25 | 16 | 13 | 13 |

TABLE X

Surfactant $H(OC_3H_6)_{12.9}-O-(C_2H_4O)_{136.4}-(C_3H_6O)_{12.9}H$
Representative of Type 2 compounds described hereinbefore

| Hydro-carbon | Volume of Hydro-carbon (ml) | Surfactant Con-centration % w/v AQ | Removal % Ethanol | % Iso-propanol | % Butanol |
|---|---|---|---|---|---|
| n-heptane | 10 | 0.25 | 36 | 38 | 36 |
| n-heptane | 3 | 0.25 | 26 | 20 | 22 |

TABLE XI

Surfactant $H(OC_3H_6)_{15.5}-O-(C_2H_4O)_{163.6}-(C_3H_6O)_{15.5}H$
Representative of Type 2 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| n-heptane | 5 | 0.5 | 34 | 36 | 34 |
| n-heptane | 0.1 | 0.25 | 36 | 31 | 46 |
| toluene | 1 | 0.25 | 26 | 24 | 22 |

TABLE XII

Surfactant $H(OC_3H_6)_{21.6}-O-(C_2H_4O)_{14.2}-(C_3H_6O)_{21.6}H$
Representative of Type 2 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| n-heptane | 10 | 0.25 | 36 | 31 | 46 |
| n-heptane | 5 | 0.5 | 36 | 36 | 35 |
| n-heptane | 0.1 | 0.25 | 26 | 22 | 27 |
| gasoline | 1 | 0.25 | 17 | 15 | 14 |
| furnace oil | 1 | 0.25 | 16 | 14 | 18 |

TABLE XIII

Surfactant $H(OC_3H_6)_{21.6}-O-(C_2H_4O)_{56.8}-(C_3H_6O)_{21.6}H$
Representative of Type 2 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| n-heptane | 5 | 0.5 | 36 | 27 | 35 |
| gasoline | 1 | 0.25 | 13 | 14 | 15 |

TABLE XIV

Surfactant $H(OC_3H_6)_{22}-O-(C_2H_4O)_{39.1}-(C_3H_6O)_{22}H$
Representative of Type 2 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| gasoline | 1 | 0.25 | 13 | 12 | 15 |

TABLE XV

Surfactant $H(OC_3H_6)_{23.4}-O-(C_2H_4O)_{15.5}-(C_3H_6O)_{23.4}H$
Representative of Type 2 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| n-heptane | 10 | 0.25 | 30 | 38 | 33 |
| gasoline | 1 | 0.25 | 8 | 10 | 13 |
| furnace oil | 1 | 0.25 | 16 | 14 | 16 |

TABLE XVI

Surfactant 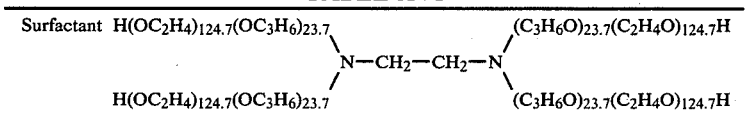

Representative of Type 3 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| n-heptane | 10 | 0.25 | 43 | 35 | 49 |
| n-heptane | 10 | 0.1 | 4 | 3 | 13 |
| n-heptane | 0.1 | 0.25 | 28 | 25 | 29 |
| gasoline | 1 | 0.25 | 13 | 14 | 14 |
| diesel oil | 1 | 0.25 | 22 | 18 | 20 |
| furnace oil | 1 | 0.25 | 8 | 12 | 14 |
| toluene | 1 | 0.25 | 23 | 22 | 19 |

TABLE XVII

Surfactant 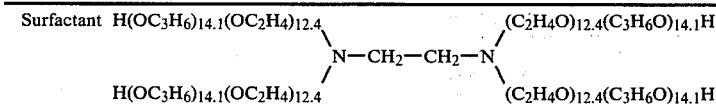

Representative of Type 4 compounds described hereinbefore

| Hydrocarbon | Volume of Hydrocarbon (ml) | Surfactant Concentration % w/v AQ | Removal % Ethanol | % Isopropanol | % Butanol |
|---|---|---|---|---|---|
| n-heptane | 1 | 0.25 | 15 | 16 | 23 |

TABLE XVIII

Surfactant: $(C_{17}H_{35}CO)-O-(C_2H_4O)_9H$
Representative of Type 5 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| dodecane | 1 | 0.25 | 6 | <1 | 5 |

TABLE XIX

Surfactant: $(C_{17}H_{35}CO)-O-(C_2H_4O)_{10}H$
Representative of Type 5 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| dodecane | 1 | 0.25 | 14 | 6 | <1 |

TABLE XX

Surfactant: $R-O-(C_2H_4O)_{12}H$
Representative of Type 5 compounds described hereinbefore
wherein R is a tall oil acid mixture
having the following approximate composition:

| Acid | % |
|---|---|
| Oleic | 24 |
| Linoleic | 19 |
| Conjugated | 4 |
| Abietic | 14 |
| Neoabietic | 7 |
| Related rosin acids | 26 |
| Unknown | 6 |

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| dodecane | 1 | 0.25 | 9 | 6 | 4 |

TABLE XXI

Surfactant: $R-O-(C_2H_4O)_{15}H$
Representative of Type 5 compounds described hereinbefore
wherein R is a tall oil acyl mixture
having the following approximate composition:

| Acid | % |
|---|---|
| Oleic | 24 |
| Linoleic | 19 |
| Conjugated linoleic | 4 |
| Abietic | 14 |
| Neoabietic | 7 |
| Related rosin acids | 26 |
| Unknown | 6 |

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| toluene | 1 | 0.25 | 14 | 10 | 16 |

TABLE XXII

Surfactant: $R-O-(C_2H_4O)_{16}H$
Representative of Type 5 compounds described hereinbefore
wherein R is a tall oil acyl mixture
having the following approximate composition:

| Acid | % |
|---|---|
| Oleic | 24 |
| Linoleic | 19 |
| Conjugated linoleic | 4 |
| Abietic | 14 |
| Neoabietic | 7 |
| Related rosin acids | 26 |
| Unknown | 6 |

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| dodecane | 1 | 0.25 | 11 | 7 | 6 |

TABLE XXIII

Surfactant: $(C_{17}H_{35}CO)-O-(C_2H_4O)_{4.5}-CO_2-C_{17}H_{35}$
Representative of Type 5 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| n-heptane | 10 | 0.25 | 9 | 1 | 21 |

TABLE XXIV

Surfactant:
$$C_{17}H_{35}-N\begin{matrix}(C_2H_4O)_{2.5}H \\ (C_2H_4O)_{2.5}H\end{matrix}$$

Representative of Type 6 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| Toluene | 1 | 0.25 | 9 | 3 | 10 |

TABLE XXV

Surfactant:
$$\begin{matrix}CH_2-O-[(C_2H_4O)(C_3H_6O)]_{8.4}H \\ | \\ CH-O-[(C_2H_4O)(C_3H_6O)]_{8.4}H \\ | \\ CH_2-O-[(C_2H_4O)(C_3H_6O)]_{8.4}H\end{matrix}$$

Representative of Type 7 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| dodecane | 1 | 0.25 | 10 | 10 | 13 |
| n-heptane | 10 | 1.0 | 43 | 45 | 47 |
| n-heptane | 5 | 0.50 | 28 | 29 | 25 |
| n-heptane | 1 | 0.25 | 28 | 28 | 25 |
| toluene | 1 | 0.25 | 26 | 25 | 24 |
| toluene | 0.5 | 0.25 | 10 | 8 | 10 |
| gasoline | 1 | 0.25 | 13 | 13 | 16 |
| furnace oil | 1 | 0.25 | 12 | 13 | 16 |

TABLE XXVI

Surfactant:
$$\begin{matrix}CH_2-O-[(C_2H_4O)(C_3H_6O)]_{14.6}H \\ | \\ CH-O-[(C_2H_4O)(C_3H_6O)]_{14.6}H \\ | \\ CH_2-O-[(C_2H_4O)(C_3H_6O)]_{14.6}H\end{matrix}$$

Representative of Type 7 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| dodecane | 1 | 0.25 | 5 | 7 | 11 |
| n-heptane | 5 | 0.5 | 26 | 27 | 27 |
| n-heptane | 0.3 | 0.25 | 26 | 21 | 22 |
| furance oil | 1 | 0.25 | 16 | 12 | 16 |

TABLE XXVII

Surfactant: 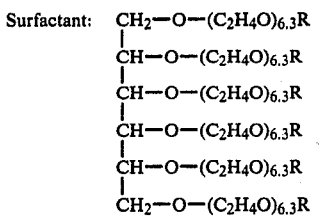

Representative of Type 8 compounds described hereinbefore wherein R is a tall oil acid mixture having the following approximate composition:

| Acid | % |
|---|---|
| Oleic | 24 |
| Linoleic | 19 |
| Conjugated linoleic | 4 |
| Abietic | 14 |
| Neoabietic | 7 |
| Related rosin acids | 26 |
| Unknown | 6 |

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| n-heptane | 1 | 0.25 | 3 | 4 | 11 |

TABLE XXVIII

Surfactant: 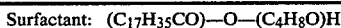
Representative of Type 9 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| n-heptane | 10 | 0.25 | 19 | 14 | 34 |
| n-heptane | 10 | 0.1 | 9 | 1 | 20 |

TABLE XXIX

Surfactant:

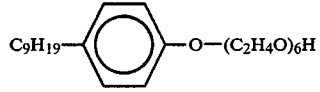

Representative of Type 9 compounds described hereinbefore

| Hydro-carbon | Volume of Hydrocarbon (ml) | Surfactant Concentration % w/v AQ | Removal | | |
|---|---|---|---|---|---|
| | | | % Eth-anol | % Isopro-panol | % Bu-tanol |
| decane | 1 | 0.25 | 11 | 7 | 11 |
| dodecane | 1 | 0.25 | 9 | 7 | 5 |

What is claimed is:

1. A method for obtaining a mixture of an alcohol and a petroleum type hydrocarbon, comprising:
mixing a fermentation solution containing water and one or more alcohols selected from the group consisting of ethanol, isopropyl alcohol and n-butyl alcohol with a mixture of a petroleum type of hydrocarbon and a compound containing a mixture of multiple polyoxyalkylene units for a time sufficient to extract said alcohol from said fermentation solution into said mixture;
and separating excess water of said fermentation solution from said mixture containing the extracted alcohol.

2. The method of claim 1 wherein the fermentation solution contains butanol.

3. The method of claim 1 wherein said compound is polyethylene glycol with an average molecular weight between 200 and 8,000.

4. The method of claim 1 wherein said compound is polypropylene glycol with an average molecular weight between 200 and 12,500.

5. The method of claim 1 wherein said compound is defined by the formula

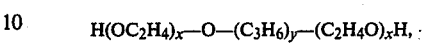

wherein x is an average number from 2.3 to 16.9 and y is an average number from 31 to 69.

6. The method of claim 1 wherein said compound is defined by the formula

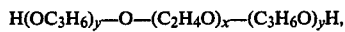

wherein x is an average number from 14.2 to 163.6 and y is an average number from 12.9 to 23.4.

7. The method of claim 1 wherein said compound is

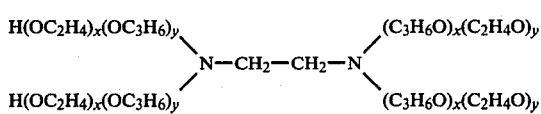

wherein x is an average number between 1 and 125 and y is an average number between 4 and 33.

8. The method of claim 1 wherein said compound is defined by the formula

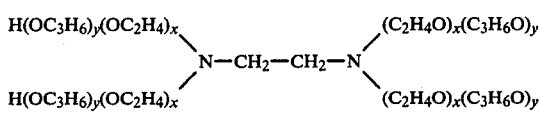

where x may vary from 1 to 30 and y may vary from 4 to 33.

9. The method of claim 1 wherein said compound is defined by the formula

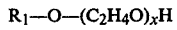

wherein x is a number from 4.5 to 16 and $R_1$ is selected from the group consisting of $C_{17}H_{35}C=O$ and a tall oil acyl mixture having the following approximate composition:

| Acid | % |
|---|---|
| Oleic | 24 |
| Linoleic | 19 |
| Conjugated | 4 |
| Abietic | 14 |
| Neoabietic | 7 |
| Related Rosin Acids | 26 |
| Unknown | 6 |

10. The method of claim 1 wherein said compound is

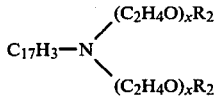

where x has an average value between 2 and 10, $R_1$ is an alkane group having up to 18 C atoms and $R_2$ is H or an alkane having up to about 18 C atoms.

11. The method of claim 1 wherein said compound is defined by the formula

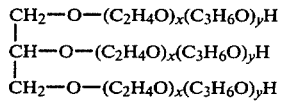

wherein the sum of x and y is a number from 3 to 18.

12. The method of claim 1 wherein said compound is

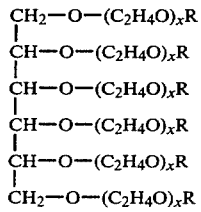

wherein R is a tall oil acid acyl mixture having the following approximate composition

| Acid | % |
|---|---|
| Oleic | 24 |
| Linoleic | 19 |
| Conjugated | 4 |
| Abietic | 14 |
| Neoabietic | 7 |
| Related Rosin Acids | 26 |
| Unknown | 6 | and x is a variable average number between 1 and 25.

13. The method of claim 1 wherein said compound is

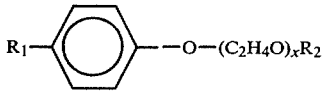

where x has a value between 2 and 100, $R_1$ and $R_2$ may be H, an alkane group or $CH_3CO-$ through $C_{17}H_{35}CO-$.

* * * * *